United States Patent [19]

Dow et al.

[11] Patent Number: 5,402,789
[45] Date of Patent: Apr. 4, 1995

[54] ULTRASONIC PERIPHERAL VASCULAR PROBE ASSEMBLY

[75] Inventors: Julian Dow, San Clemente; Paul F. Meyers, San Juan Capistrano; Michael Waddell, San Clemente, all of Calif.

[73] Assignee: Capistrano Labs, Inc., San Clemente, Calif.

[21] Appl. No.: 188,482

[22] Filed: Jan. 28, 1994

Related U.S. Application Data

[63] Continuation-in-part of Ser. No. 980,583, Nov. 23, 1992, Pat. No. 5,329,194.

[51] Int. Cl.⁶ .............................................. A61B 8/00
[52] U.S. Cl. .................................................. 128/660.1
[58] Field of Search .................... 128/660.05, 660.08, 128/660.09, 660.10, 661.08, 661.09, 662.03; 73/621, 622, 629

[56] References Cited

U.S. PATENT DOCUMENTS

| | | | |
|---|---|---|---|
| 3,955,561 | 5/1976 | Eggleton | 128/2.05 |
| 4,092,867 | 6/1978 | Matzuk | 73/609 |
| 4,106,346 | 8/1978 | Matzuk | 73/614 |
| 4,149,419 | 4/1979 | Connell et al. | 63/621 |
| 4,167,180 | 9/1979 | Kossoff | 128/660.09 |
| 4,246,792 | 1/1981 | Matzuk | 73/620 |
| 4,271,706 | 6/1981 | Ledley | 73/614 |
| 4,282,879 | 8/1981 | Kunii et al. | 128/660 |
| 4,341,120 | 7/1982 | Anderson | 73/618 |
| 4,375,818 | 3/1983 | Suwaki | 128/660 |
| 4,391,282 | 7/1983 | Ando et al. | 128/660 |
| 4,398,425 | 8/1983 | Matzuk | 73/633 |
| 4,399,703 | 8/1983 | Matzuk | 73/621 |
| 4,401,123 | 8/1983 | Baba | 128/660 |
| 4,421,118 | 12/1983 | Dow et al. | 128/660 |
| 4,424,813 | 1/1984 | Havlice et al. | 128/660 |
| 4,466,443 | 8/1984 | Utsugi | 128/660 |
| 4,479,388 | 10/1984 | Matzuk | 73/634 |
| 4,483,326 | 11/1984 | Yamaka et al. | 128/4 |
| 4,545,117 | 1/1985 | Okamoto | 29/596 |
| 4,584,880 | 4/1986 | Matzuk | 73/609 |
| 4,646,722 | 3/1987 | Silverstein | 128/4 |
| 4,674,515 | 6/1987 | Andou et al. | 128/660 |
| 4,675,563 | 6/1987 | Goldowsky | 310/15 |
| 4,722,345 | 2/1988 | Ueno et al. | 128/660 |
| 4,756,313 | 7/1988 | Terwilliger | 128/660 |
| 4,785,819 | 11/1988 | Pearce | 128/660.10 |
| 4,831,292 | 5/1989 | Berry | 310/15 |
| 4,841,979 | 6/1989 | Dow et al. | 128/660.10 |
| 4,850,362 | 7/1989 | Rello et al. | 128/660.05 |
| 4,893,628 | 1/1990 | Angelsen | 128/660.05 |
| 4,913,155 | 4/1990 | Dow et al. | 128/660.1 |
| 4,930,515 | 6/1990 | Terwilliger | 128/662.06 |
| 5,012,147 | 4/1991 | Bertram et al. | 310/80 |
| 5,048,529 | 9/1991 | Blumenthal | 128/660.1 |
| 5,085,221 | 2/1992 | Ingebrigtsen | 128/660.1 |
| 5,088,495 | 2/1992 | Miyagawa | 128/660.1 |
| 5,111,092 | 5/1992 | Reinicke | 310/68 B |
| 5,165,413 | 11/1992 | Maslak et al. | 128/660.05 |

Primary Examiner—George Manuel
Attorney, Agent, or Firm—Stetina Brunda & Buyan

[57] ABSTRACT

An ultrasonic probe has a housing, a base pivotally mounted within the housing, an extension formed upon the base, and a scanning ultrasonic transducer disposed upon the distal end of the extension. The extension is preferably configured such that the scanning transducer moves along an arc of approximately 50 degrees having a radius of approximately 40 mm and is thus suitable for imaging elongate anatomical structures such as portions of the peripheral vascular system. A doppler ultrasonic transducer optionally fixedly disposed within the housing proximate the scanning ultrasonic transducer measures fluid flow within the elongate anatomical structure. The doppler ultrasonic transducer is disposed at one end of the arc along which the scanning ultrasonic transducer travels such that the radiation path of the doppler ultrasonic transducer is periodically obscured by the scanning ultrasonic transducer. The doppler ultrasonic transducer measures fluid flow through the elongate anatomical structure when the scanning ultrasonic transducer is not within the radiation path of the doppler ultrasonic transducer.

9 Claims, 5 Drawing Sheets

ULTRASONIC PERIPHERAL VASCULAR PROBE ASSEMBLY

RELATED APPLICATIONS

The subject patent application is a continuation-in-part patent application of United States Ser. No. 07/980,583, filed on Nov. 23, 1992, now U.S. Pat. No. 5,329,194, and entitled ULTRASONIC PERIPHERAL VASCULAR PROBE ASSEMBLY, the contents of which are hereby incorporated by reference.

FIELD OF THE INVENTION

The present invention relates generally to ultrasonic probe assemblies for use in real-time diagnostic imaging and relates more specifically to an ultrasonic probe assembly for real-time imaging of elongate anatomical structures.

BACKGROUND OF THE INVENTION

In the field of ultrasonic diagnostics, acoustic images of anatomical structures are utilized in the diagnosis of various medical disorders. In order to produce real-time images of the anatomic structures, beams of ultrasonic energy from a probe are transmitted into the body tissue of a patient and echoes received by the ultrasonic probe are rapidly processed into an image format suitable for display. It is desirable that the probe produce an image over a wide field of view using a sector scan format. A sector scan format generates an image by repeatedly transmitting and receiving ultrasonic energy in radial directions away from the probe to define a fan-like pattern. The ultrasonic beam is directed by mechanically moving an ultrasonic transducer such that it is swept through an arc about a pivot axis to produce the fan-like sector scan pattern.

The prior art is replete with examples of ultrasonic transducer probe assemblies, such as those disclosed in U.S. Pat. No. 4,149,419 entitled "Ultrasonic Transducer Probe" issued Apr. 17, 1979 to R. Connell et al.; U.S. Pat No. 3,955,561 entitled "Cardioscan Probe" issued May 17, 1976 to R. Eggleton; U.S. Pat. No. 4,421,118 entitled "Ultrasonic Transducer" issued Dec. 20, 1983 to J. Dow et al.; U.S. Pat No. 4,479,388 entitled "Ultrasonic Transducer and Drive System" issued on Oct. 30, 1984 to T. Matzuk; U.S. Pat. No. 4,399,703 entitled "Ultrasonic Transducer and Integral Drive Circuit Therefor" issued on Aug. 23, 1983 to T. Matzuk; U.S. Pat No. 4,092,867 entitled "Ultrasonic Scanning Apparatus" issued on Jun. 6, 1978 to T. Matzuk; U.S. Pat. No. 4,246,792 entitled "Self-Contained Ultrasonic Scanner" issued Jan. 27, 1981 to T. Matzuk; U.S. Pat. No. 4,398,425 entitled "Ultrasonic Scanning Transducer" issued on Aug. 16, 1983 to T. Matzuk; U.S. Pat No. 4,841,979 entitled "Ultrasonic Prostate Probe Assembly" issued on Jun. 27, 1989 to Dow et al.; and U.S. Pat. No. 4,913,155 entitled "Ultrasonic Transducer Probe Assembly" issued on Apr. 3, 1990 to Dow et al.

Although all of the above-referenced patent disclosures address various problems associated with the use of ultrasonic transducer imaging, none have addressed the particular problems associated with the use of an ultrasonic transducer probe for the imaging of elongate anatomical structures such as blood vessels in the peripheral vascular system. Furthermore, none of the cited patent disclosures address the problem of measuring fluid flow through such an elongate anatomical structure while simultaneously providing real-time imaging of the structure.

It would be desirable to provide real-time imaging of elongate portions of the peripheral vascular system and simultaneous measurements of the flow of blood therethrough. More particularly, it would be beneficial to provide real-time imaging of the carotid artery while simultaneously measuring the flow of blood therethrough in order to determine the presence of any pathologies, abnormal structures or conditions, and/or any indication of problems elsewhere within the vascular system, i.e., as provided by the blood flow rate.

Prior art ultrasonic probe assemblies have been ineffective in providing a satisfactory means for real-time imaging of elongate anatomical structures such as portions of the peripheral vascular system due to the sharp radius of curvature followed by the ultrasonic transducers thereof and additionally due to their inability to provide simultaneous blood flow measurements. The use of such a sharp radius of curvature is inherent in prior art devices due to the mounting of the ultrasonic transducer in immediate proximity to the pivot axis thereof. That is, the radius of the arc traveled by the ultrasonic transducer in such prior art devices is typically approximately 5-10 centimeters in length. Thus, the path traveled by the ultrasonic transducer is sharply curved and consequently suitable only for the imaging of comparatively small areas.

As such, although the prior art has recognized to a limited extent the problem ultrasonically imaging portions of the human anatomy, the proposed solutions have to date been ineffective in providing a satisfactory remedy.

SUMMARY OF THE INVENTION

The present invention specifically addresses and alleviates the above-mentioned deficiencies associated in the prior art. More particularly, the present invention comprises an ultrasonic probe having a housing, a base pivotally mounted within the housing, an extension formed upon the base, and a first or scanning ultrasonic transducer disposed upon the distal end of the extension. The extension is preferably configured such that the scanning ultrasonic transducer moves along an arc of approximately 50 degrees having a radius of approximately 40 mm and an arc length of approximately 35 mm.

The imaging ultrasonic transducer is disposed within a narrow housing or head which allows the user to easily manipulate the device so as to locate and rotate the device in order to follow elongate anatomical structures.

Thus, the present invention is especially well suited for the ultrasonic imaging of elongate anatomic structures such as peripheral blood vessels and the like. However, although the ultrasonic peripheral vascular probe assembly of the present invention is particularly well suited for imaging and blood flow measurement of peripheral blood vessels such as the carotid artery, those skilled in the art will recognize that it is likewise suited for imaging and blood flow measurement of various other anatomical structures, including those which are not elongate in configuration.

A second or doppler ultrasonic transducer 155 is fixedly disposed within the housing proximate the first ultrasonic transducer and utilizes the doppler effect to measure fluid flow within anatomical structures. The doppler ultrasonic transducer 155 is preferably disposed at one end of the arc along which the scanning ultrasonic transducer travels and thus the scanning ultrasonic transducer periodically obscures the radiation path of the doppler ultrasonic transducer 155. Such positioning of the doppler ultrasonic transducer 155 thus minimizes the size of the probe. The doppler ultrasonic transducer 155 consequently measures fluid flow through the anatomical structure being imaged only when the scanning ultrasonic transducer is not within the radiation path of the doppler ultrasonic transducer 155.

The imaging ultrasonic transducer is pivoted by a linear motor having an electrical coil as the reciprocally moving member. The coil is in a plane orthogonal to the lines of flux between opposed permanent magnets of opposite polarity affixed to the probe case, thereby providing improved efficiency. A mechanical linkage between the linear motor electrical coil moving member and the transducer, which is forced in pivoting motion, transmits only axial force, not torque, by employing a ball and socket joint at one end of the crank shaft. Electrical connections to the electrical coil are facilitated through springs which additionally mechanically bias the reciprocal movement of the coil. Electrical connections to the pivoting transducer are facilitated through a helical coil wrapping the pivot shaft. These electrical connections accommodate mechanical motions within the probe. A bellows-fold, cylindrical air bladder is positioned within the fluid chamber of the probe to allow for thermally-induced changes in fluid volume.

These, as well as other advantages of the present invention, will be more apparent from the following description and drawings. It is understood that changes in the specific structure shown and described may be made within the scope of the claims without departing from the spirit of the invention.

Detailed Description of the Preferred Embodiment

The detailed description set forth below in connection with the appended drawings is intended as a description of the presently preferred embodiment of the invention, it is not intended to represent the only form in which the present invention may be constructed or utilized. The description sets forth the functions and sequence of steps for constructing and operating the invention in connection with the illustrated embodiment. It is to be understood, however, that the same or equivalent functions or sequences may be accomplished by different embodiments that are also intended to be encompassed within the spirit and scope of the invention.

Figures 1, 2, 3, 4, 5:
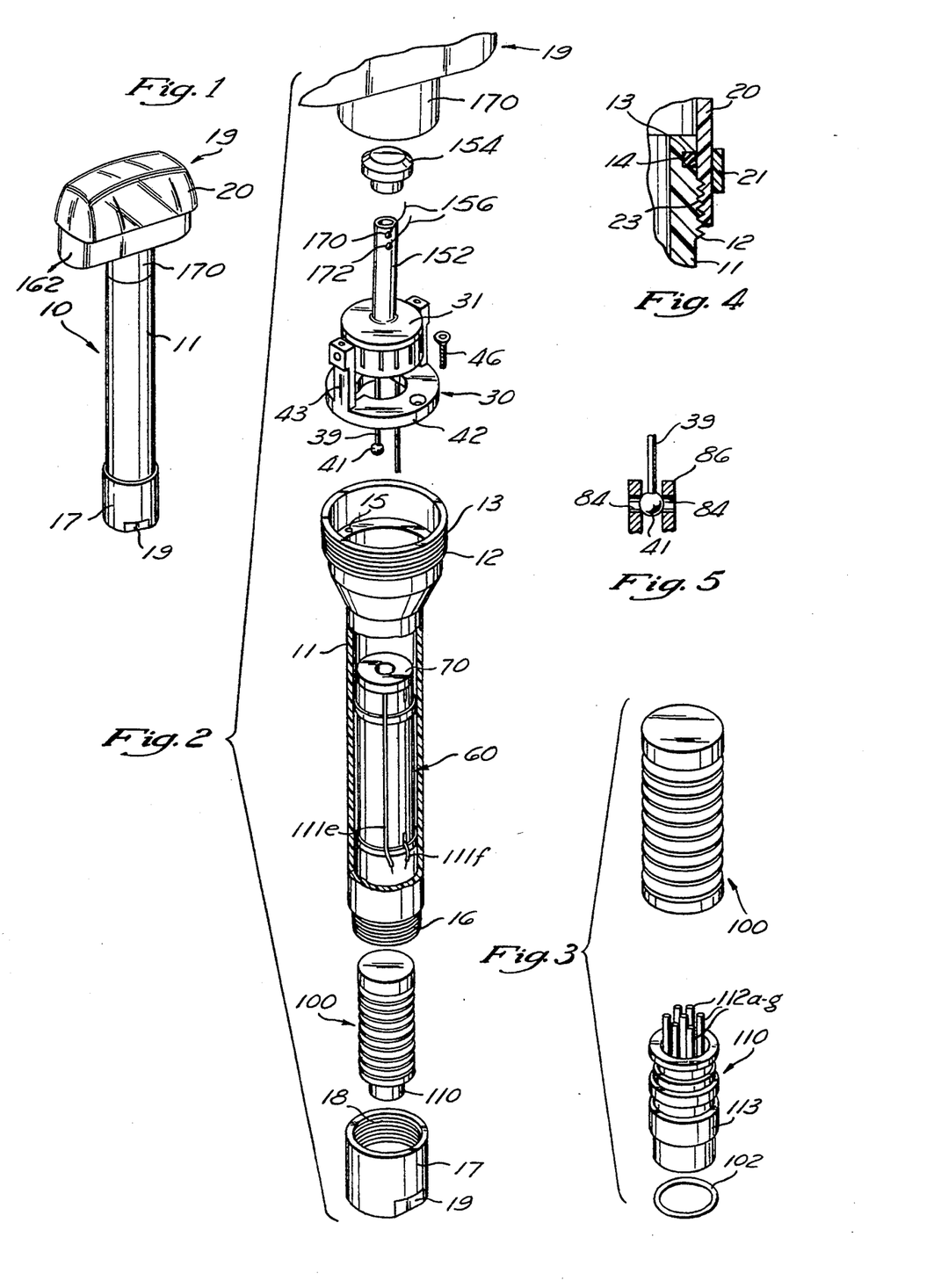
FIG. 1 is a perspective view showing the preferred embodiment ultrasonic transducer probe assembly in accordance with the present invention.
FIG. 2 is an exploded view, partially in cross-section, showing major functional elements in the ultrasonic transducer probe assembly.
FIG. 3 is an exploded view particularly showing the air bladder and the electrical connector elements of the ultrasonic transducer probe assembly.
FIG. 4 is a partial cross-sectional view showing the threaded interconnection of the acoustic cone to the case of the ultrasonic transducer probe assembly.
FIG. 5 is an enlarged view, partially in cross-section, showing the detailed mechanical connection of a crankshaft to the upper extension of a moving coil within a linear motor assembly of the ultrasonic transducer probe assembly.

The present invention is embodied within an ultrasonic transducer probe assembly 10 which is depicted in FIGS. 1-16 of the drawings. Referring now to FIG. 1, an ultrasonic transducer probe 10 constructed in accordance with the principles of the present invention, is shown in perspective view. The probe elements are housed in a case 11, which may be machined from aluminum, or which may be molded of derin, polysulfone, or similar material. A lower sleeve 17 at one end of case 11 defines an aperture (not shown) through which cabled connection is made via a cable (not shown) to power supplies, signal generators, and signal processors which are employed in use with the probe for ultrasonic imaging. An acoustic cone or cap 20 is fitted at the end of the case. The cap 20 is made of polyethylene or other material which is highly transmissive to ultrasound. During use, ultrasonic energy passes through the cap 20 to and from an ultrasonic transducer 31 by way of the intervening fluid 22 inside the probe. The fluid 22 is a non-toxic liquid, such as a Siloxane based oil, which acts as both a lubricant and ultrasound couplant. As best seen in FIG. 4, the acoustic cap 20 has interior threads 23 which mate with complementary threads 12 around the periphery of the open end of the case 11, and is sealed in place by a plastic compression band 21. This seal is made fluid-tight by an O-ring 14 which is compressed in groove 13 between the cap 20 and the case 11.

Figure 6:
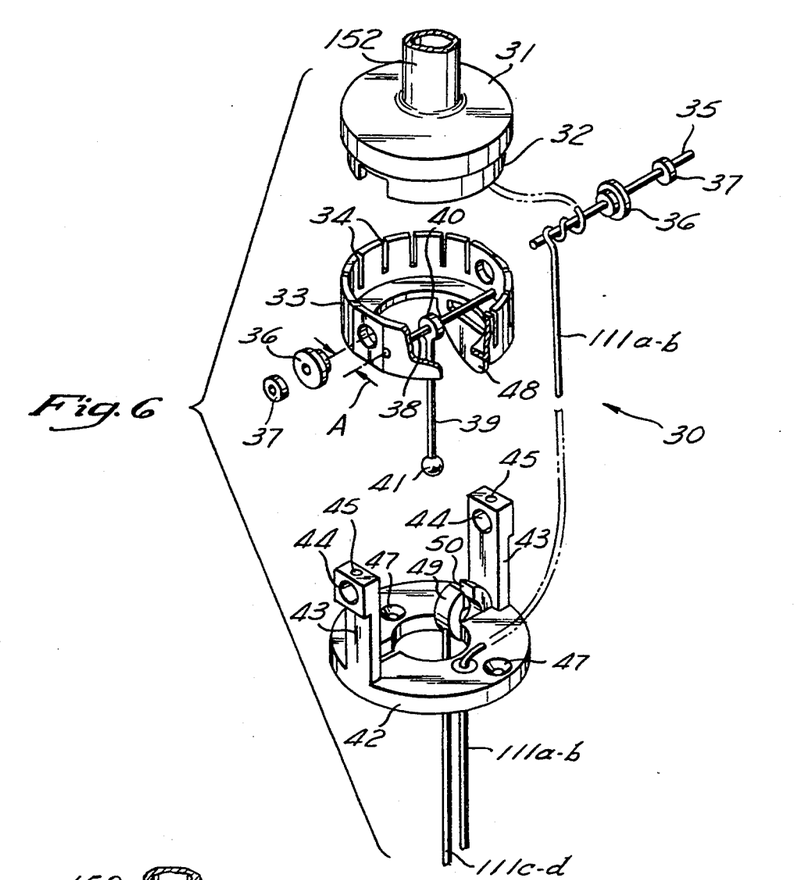
FIG. 6 is an exploded perspective view showing the transducer mounting assembly element within the ultrasonic transducer probe assembly.
Figure 7:
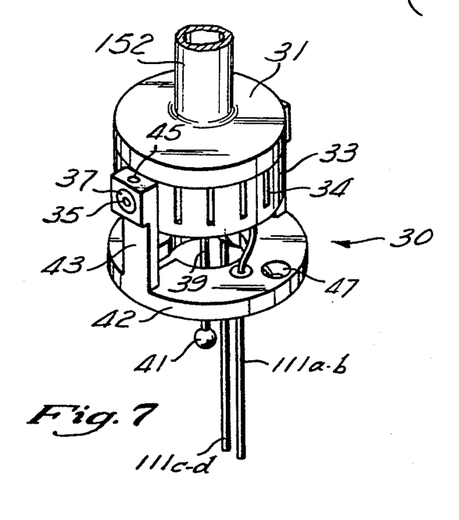
FIG. 7 is an assembled perspective view of the same transducer mounting assembly element previously seen in FIG. 6.
Figure 8:
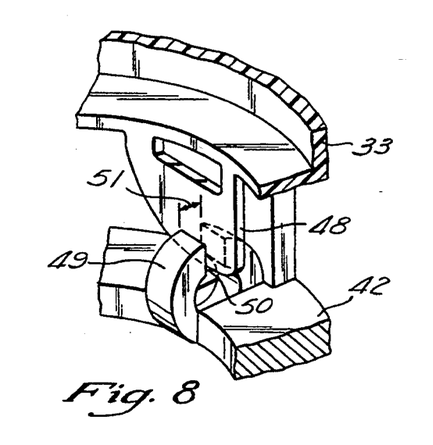
FIG. 8 is a perspective view showing the detailed structure of a flange upon a transducer cup, which flange passes through a gap within a position-sensing toroidal coil upon a gimbal cup in order that the tilt of the transducer, within the ultrasonic transducer assembly in accordance with the present invention, may be definitively known.

As may be observed in FIGS. 2, 6, and 7, the transducer 154 is disposed upon an extension 152 which is formed upon base 31, which, in turn, is seated in a ring 32. The ring 32 then snaps into place in a cup 33. This snapping is facilitated by a slight expansion in cup 33 permitted by axial slots 34 formed therein. This permits incorporating, during manufacture, a variety of transducers and/or extensions of different characteristics, each of which fits rings of the same outer dimension. When a customer orders a probe with a specified transducer or extension configuration, then the selected transducer, extension, and ring module can be snapped into the cup and the necessary electrical connections can be made.

The transducer cup 33 contains ball-bearing fittings 36 on either side, with a hard steel axle pin 35 passing therethrough. A stainless steel crank pin 38 is press-fit through the transducer cup 33 parallel to the axle pin 35. In a preferred embodiment of the present invention, the crank pin 38 is spaced apart from the axle pin 35 by a distance A of approximately 0.090 inch. This nominal spacing is one of the determining factors of the angle through which the transducer 31 is pivoted. In the preferred embodiment, the oscillation angle is 50 degrees. A one-thousandth of an inch variation in the spacing distance corresponds to approximately a one-degree variation in the oscillation angle.

As may be best observed in FIG. 6, one end of the crankshaft 39 is connected to the crank pin 38 in a bearing 40. The other end of the crankshaft 39 is connected to the moving coil assembly 80 of the linear motor assembly 60 in a ball and socket joint. This joint, shown in detail in FIG. 5, consists of the ball 41 at the end of crankshaft 39 (observable in FIG. 6) and the socket defined by holes 84 at the upper extension 86 to coil assembly 81 of moving coil assembly 80 (observable in FIGS. 9 and 10).

The crankshaft 39 will not transmit torque, or angular motion, between the moving coil assembly 80 and the linear motor assembly 60 which it connects. In the preferred embodiment, this is because of the ball and socket joint, which joint could have equally as well been located at the other end of crankshaft 39. Alternatively, it should be recognized that crankshaft 39 could itself incorporate a rotary joint. Alternatively, other means well known in the art (such as hydraulics) for transmitting axial force without torque could have been used to couple the driving member of moving coil assembly 80 to the driving member of transducer 31.

Continuing in FIG. 6, the ends of the axle pin 35 which extend from the cup 33 are located in bearings 37 in holes 44 in arms 43 which extend from the base of a gimbal cup 42. The bearings 37 are held firmly in the holes 44 in the gimbal cup arms 43 by orthogonally-directed set screws 45 in the gimbal cup arms 43. Referencing FIG. 2, the gimbal cup 42 is held in place in the case 11 by screws 46, which pass through holes 47 in the gimbal cup 42 and into threaded holes 15 in the case 11. The base of the gimbal cup 42 fits against the upper plug 70 to the linear motor assembly 60.

The complete transducer mounting assembly 30 is illustrated in FIG. 7. In accordance with the present invention, the transducer mounting assembly 30 is capable of providing a sensor output which is indicative of the precise instantaneous angle that transducer 31 is tilted about pivot shaft 35. This sensor output is obtained from position-sensing toroidal coil 49, shown in FIG. 6 and further in expanded view in FIG. 8. The toroidal coil 49 is affixed within slot 50 within the base of the gimbal cup 42. The gap 51 of this toroidal coil 49 is variably entered by flange 48 of the transducer cup 33, dependent upon how much this transducer cup 33, and the transducer 31 mounted therein, are tilted about the axis defined by pivot shaft 35. The contours of flange 48 are such that a variable amount of metal, nominally a ferrous metal, will be rotated, i.e., pass within the gap 51 of toroidal coil 49, in response to a corresponding variable tilt angle of the transducer 31. This amount of metal changes the inductance of toroidal coil 49 in a manner which may be sensed by interconnected electronics circuitry (not shown). Accordingly, the toroidal coil 49, which is variably entered in its gap 51 by flange 48, constitutes a sensor of the angular tilt of transducer 31.

Figures 9, 10, 11:
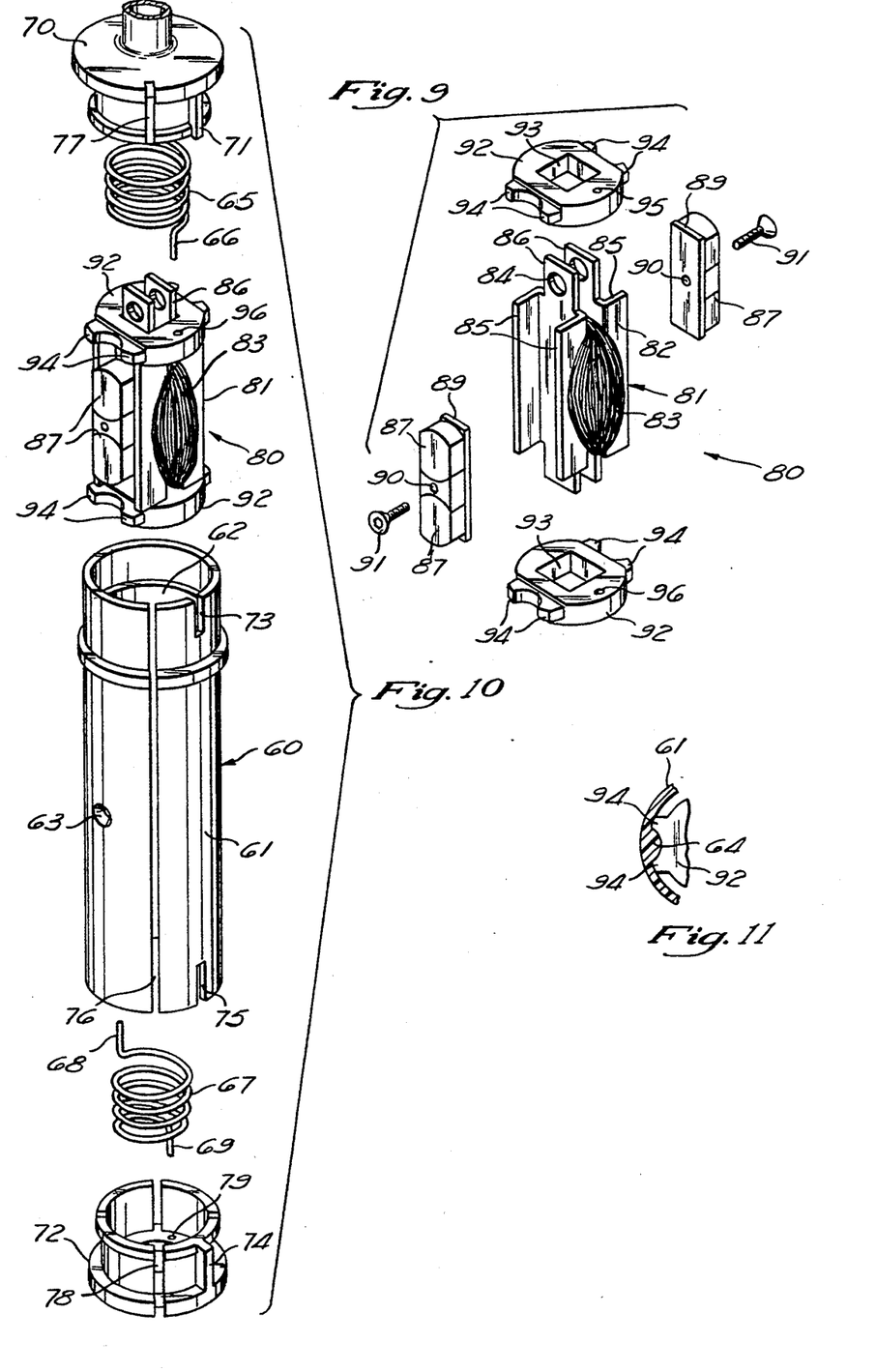
FIG. 9 is an exploded perspective view showing the armature of the linear motor assembly in accordance with the present invention.
FIG. 10 is an exploded perspective view showing the linear motor assembly of the ultrasonic transducer probe assembly.
FIG. 11 is a detailed perspective view showing the connection of a moving magnet assembly in the region of certain guide portions thereof to a metal sleeve assembly.
Figure 12:
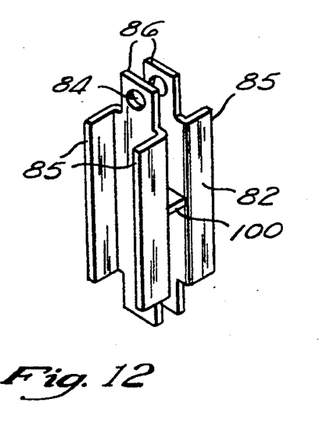
FIG. 12 is an enlarged view showing a frame around which coil wire is wrapped to form a moving coil assembly part of the linear motor assembly within the ultrasonic transducer probe assembly.

The linear motor 50, which is shown to be located within case 11 in FIG. 1, is further shown in exploded view in FIG. 10. An upper plug 70 is press-fit to the top of composite metal sleeve assembly 61 so that guide ridge 71 fits into radial guide slot 73. Likewise, lower plug 72 is press-fit to the bottom of sleeve assembly 61 so that guide ridge 74 fits into radial guide slot 75. Between the upper plug 70 and the lower plug 72 and within the sleeve assembly 61 is an upper compression spring 65, a motor subassembly 80, and a lower compression spring 67. The motor subassembly 80 includes permanent magnets 87, moving armature coil 81, and those miscellaneous parts which are all illustrated in exploded view in FIG. 9. The permanent magnets 87 are secured to sleeve assembly 61 by machine screws 91 which slip both holes 63 in sleeve 61 and holes 90 in the permanent magnets 87 in order to threadingly engage backing plates 89 to which the magnets 87 are permanently affixed. While the magnets 87 remain fixed to sleeve 61, the retaining parts of motor subassembly 80 (shown in FIG. 9) slide axially in sleeve 61.

The drive motor for the ultrasonic peripheral vascular probe assembly of the present invention is described in U.S. Pat. No. 4,913,155, issued on Apr. 3, 1990, and entitled ULTRASONIC TRANSDUCER PROBE ASSEMBLY, the contents of which are hereby incorporated by reference.

Figure 14:
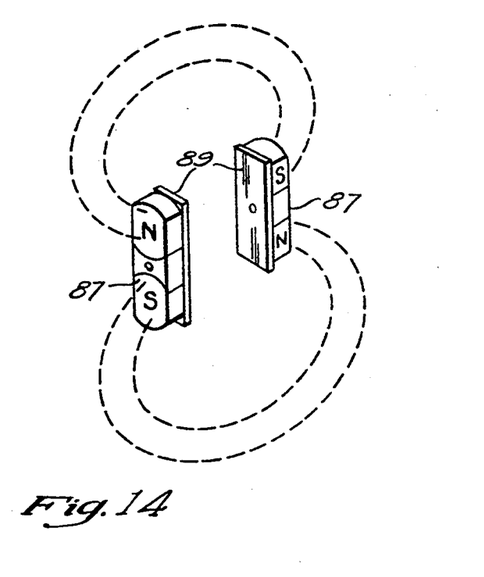
FIG. 14 is a diagrammatic representation showing the field lines of magnetic flux created by the opposed permanent magnets within the linear motor assembly.

Referencing FIG. 9, the motor subassembly 86 includes moving armature coil 81. A coil of wire 83 is wrapped about an H-frame 82 which is illustrated in isolation in FIG. 12. The wire coil 83 is substantially in a plane which is defined by and which is perpendicular to the plane of the center portion 100 of H-frame 82. It may be observed in FIG. 9 that this plane is orthogonal to a straight line between oppositely disposed magnets 87. The North, or "N", and South, or "S", poles of the two magnets 87 are in opposite orientation as illustrated in FIG. 14. Consequently, the lines of magnetic force, or flux, between the magnets 87 are substantially as illustrated in FIG. 14. The plane of moving armature coil 81, and particularly of wire coil 83 therein, may be observed to be substantially orthogonal to the field lines of magnetic flux between the permanent magnets 87.

Continuing in FIG. 9, the "H" frame 82 includes a pair of guide flanges 85. These guide flanges 82 are oriented as partial chords to the circular cross-section of bore 62 to sleeve 61 (shown in FIG. 10). The guide flanges 85 define U-channels within which the magnets 87 and the magnets' backing plates 89 will slide without substantial contact. A substantially central position of moving armature coil 81 within motor subassembly 80 and within the entire linear motor 60 is established by (i) the substantially equal displacement of end guides 92 respectively from upper plug 70 and lower plug 72 by (ii) action of substantially equal strength springs 65 and 67 (all shown in FIG. 10). The frame 82 further has upper extension 86 defining holes 84. The extensions, including upper extension 86, of coil frame 82 pass through the substantially square apertures 93 of the end guides 92. These end guides 92 are made of an insulating plastic which exhibits low frictional resistance to sliding within the internal bore 62 of sleeve 61. The end guides 92 are prevented from rotating within sleeve 61 by their guide tabs 94 which engage the complementary structure of guide ridge 64 on the interior of sleeve 61, all as shown in partial cross-sectional view in FIG. 11.

Figure 13:
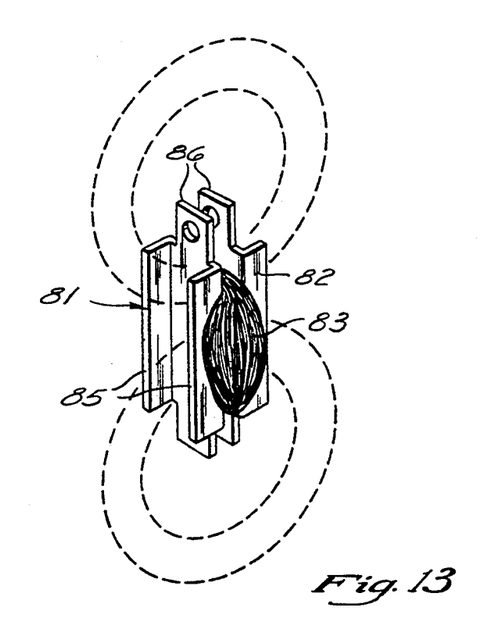
FIG. 13 is a diagrammatic representation showing the field lines of magnetic flux emanating from an energized moving coil assembly within the linear motor assembly which is part of the ultrasonic transducer probe assembly.

When the wire coil 83 is electrically energized, through a wired connection as will be explained, it produces a magnetic field which is diagrammatically illustrated in FIG. 13. The direction of magnetic flux within this magnetic field is, of course, dependent upon the direction of a current flow which is induced by a voltage of a corresponding polarity within coil 83. It may be noted that the lines of magnetic flux resultant from energization of coil 83 are similar to, and substantially coincident with, the lines of magnetic flux resultant from permanent magnets 87. This means that the flux coupling is optimal or nearly optimal, and that the linear motor 60 is efficient. Referring to FIGS. 9 and 10, the electrical energization of coil 83 will cause movement of the moving armature coil 81, coil frame 82, and end guides 92 axially within sleeve 61 and against the spring forces of springs 65 and 67. The direction of movement of motor subassembly 80, and which one of the springs 65, 67 compresses, and which one extends will be determined by the direction of current flow within coil 83.

Connection between the linear motor 60, specifically in the motor subassembly 80 and more specifically in the holes 85 of coil frame 82 (shown in FIGS. 9 and 10), and the pivotable transducer mounting assembly 30 specifically at the crank pin 38 (shown in FIG. 6), is made by crankshaft 39 (shown in FIGS. 2 and 5-7). The crankshaft 39 is affixed for rotation about crank pin 38 by bearing 40, as previously explained during discussion of FIG. 6. The other end of crankshaft 39 terminates in ball 41. This end of crankshaft 39, and its ball 41, pass through the central aperture of upper plug 70 (shown in FIG. 9). The ball 41 is retained between the holes 84 to upper extension 86 to coil frame 82, as is shown in detail in the side view of FIG. 5. This second-end connection of crankshaft 39 is thus by a ball and socket joint.

Also as previously explained during discussion of FIG. 6, this connection of crankshaft 39, in a manner which will not transmit torque, is one of the significant aspects of the present invention. Particularly, the ball and socket joint can accommodate both angular misalignment and angular variation between the pivotable transducer mounting assembly 30 and the motor assembly 80 of the linear motor 60. These variations cannot be well tolerated by a crankshaft which is pinned at both ends. It has been found that the angular alignment of crank pin 38 and of motor subassembly 80 relative to the axis of case 11 is difficult to initially establish during assembly, and to maintain during operation. In this regard, it should be noticed that end guides 92 must slide freely within sleeve 61 which is affixed to case 11. Consequently, the motor subassembly 80, and the extension 86 to the coil frame 82 therein, should be expected to twist, or rotate, very slightly in a random manner during operation. Although the pivotable transducer may be initially aligned to the linear motor, and although a rudimentary alignment is thereafter maintained, careful consideration of the forces acting on crankshaft 39, bearing 40, and crank pin 38 (which should and do exhibit low mass as reciprocating components) will reveal that axial forces only should be coupled by the crankshaft 39. The coupling of torque should be avoided within the crankshaft 39 or at the pinned ends thereof (such as at bearing fit 40). Transmission of axial forces while avoiding coupling of rotational forces is accomplished by the ball and socket joint. This joint could obviously be alternatively positioned at the transducer mounting assembly 30 end to crankshaft 39, or the joint could be replicated at both ends of crankshaft 39. Alternatively, the crankshaft itself could incorporate a rotary slip joint.

The electrical connections of the transducer are facilitated in part by the cable 111a-b which is preferably of the coaxial type. Each of the two conduits within this cable 111a-b make a first-end electrical connection, preferably by soldering, at the transducer 31. As may be best observed in FIG. 6, this cable 111a-b is wound around pivot shaft 35, forming a toroidal coil of several turns about the shaft. The cable 111a-b vectors off at a tangent to this toroidal winding in order to connect to the transducer 31 at a first end, or to be routed further into case 11 before exiting probe 10 at a second end. Inspection of this preferred manner of electrical connection via a coil about the pivot shaft, which manner of connection is shown in FIG. 6, will reveal that the tilting, or pivoting, of the transducer 31 about pivot shaft 35 results in a slight tensioning, or slight loosening, of the turns of the coiled cable 111a-b. Any undesirable counteracting torque on the pivoting of transducer 31, or any sudden releases of energy resulting in erratic angular movement and/or minute vibrations to the transducer 31, or any appreciable flexing or wearing of cable 111a-b, are almost entirely avoided by the preferred manner of its connection. This electrical connection is but part of that particular aspect of the present invention which is concerned with improved electrical routing and wired connections within an ultrasonic transducer probe.

Continuing with the electrical connections within probe 10, the cable 111c-d, shown in FIGS. 6 and 7, is nominally the extension of two wires, nominally wrapped as a twisted pair, from the two terminals of toroidal coil 49. Both the cable 111a-b and the cable 111c-d, totaling four electrical paths, are routed through the circumferential notch 77 in upper plug 70, within the axial channel 76 of sleeve 61, through the circumferential notch 78 of lower plug 72 (all shown in FIG. 10) and along the outside of air bladder 100 (shown in FIGS. 2 and 3) to terminate in connector 110 (shown in FIG. 3).

Electrical connections to coil 83 within moving armature coil assembly 81 within motor subassembly 80 are made via the springs 65, 67 which further serve to mechanically bias the movement of motor subassembly 80. Particularly, the upper spring 65 has a lower tail 66 which fits through hole 95 in the upper one of end guides 92 and thereafter connects, as a first electrical connection, to coil 83. The other end of upper spring 65 is connected, nominally by soldering, to wire 111c. This wire 111c is shown isolated from nearby wires 111a–b in FIG. 7 in order that its individual routing within axial groove 76 of sleeve 61 may be more clearly observed. The lower spring 67 has an upper tail 68 which fits through hole 96 in the lower one of end guides 92 and thereafter connects, as a second electrical connection, to coil 83. The lower spring 67 also has a lower tail 69 which fits through hole 79 in lower plug 72, arid thereafter is connected, nominally by soldering, to wire 111f which is shown in FIG. 2. This electrical connection to a moving coil element of a linear motor through the same springs which mechanically bias movement of the coil is another part of that aspect of the present invention which is concerned with improved electrical routing and wired connections in an ultrasonic transducer probe.

The cables 111a–f all extend to a point within case 11 adjacent the lower extremity of linear motor 60. Beyond this point these cables 111a–f are routed along the outside of air bladder 100 and are soldered to six of the seven through-pins 112a–g of connector body 110. The connector body 110 is watertight and its pins 112a–g are potted. It is normally of the male type, and connects to a cable (not shown) which supplies power and signal drive to, and which receives sensor outputs from, probe assembly 10.

The watertight connector body 110 has a flange 113 which engages a like feature within the central bore of lower collar 17. Between these mating surfaces is positioned an O-ring 102. When the lower collar 17 is threaded onto case 11 by the engagement of interior threads 18 with exterior threads 16, then the O-ring 102 is compressed and the entire probe assembly 10 is sealed. Tightening of the lower collar 17 to effect this seal may be aided by fitting a wrench to flat 19. The entire inside of the probe 10 from cone, or cap, 20 to connector body 110 is preferably filled with an incompressible fluid save for air bladder 100. The fluid does not interface with motion of the linear motor, nor with any electrical paths.

The air bladder 100 contains a sealed quantity of a compressible gas, preferably air, and located within the fluid reservoir defined within probe 10. The air bladder 100 is preferably in the shape of a cylinder, as illustrated, which preferably exhibits bellows-folds or pleats or, alternatively, alternating grooves and ridges circumferentially along its surface. The fluid within the reservoir of probe 10 expands with increasing temperature and contracts with decreasing temperature. Save for the compressible air bladder 100, this expansion and contraction could cause leakage within the instrument.

Fluid leakage is particularly undesirable because, as the fluid 22 leaks out, the fluid is replaced by air when the pressure within the probe 10 equalizes to outside atmospheric pressure. Once in the fluid compartment of probe 10, the air bubbles soon make their way to that upper region of the compartment where ultrasonic transducer 31 is located. When the air bubbles are located in front of the face of the ultrasonic transducer 31, then they cause problems because ultrasound energy is attenuated and scattered by air. The presence of air bubbles can thereby render the transducer probe virtually useless for diagnostic imaging.

A particularly troublesome source of fluid leakage and bubble formation is resultant from a thermal cycling of the probe 10. As the probe 10 is warmed, the fluid 22 will expand in accordance with is temperature expansion coefficient. The pressure within the fluid compartment will build and some fluid may leak out. When the probe 10 is thereafter cooled, the fluid will contract, which creates a negative pressure in the compartment relative to atmospheric pressure until air leaks in to equalize the pressure. Such thermal cycling may occur, for instance, when a probe is left in the trunk of a car on a warm day, and is then taken into an air-conditioned building.

To account for the effects of thermal cycling, the preferred embodiment probe 10, in accordance with the present invention, incorporates the air bladder 100 as an expansion chamber. The expansion chamber is a compressible part of the fluid compartment. The bellows-fold wall of the air bladder 10 expansion chamber is extensible and contractible in length, thereby readily allowing the volume of air within air bladder 100 to expand or contract. As the fluid expands and contracts, the air bladder 100 will correspondingly contract and expand to maintain the desired fluid pressure within the compartment as the fluid volume changes. Desirably, the air bladder 100 expansion chamber is at least one-fifth as large as the total fluid volume within probe 10 in order to accommodate wide variations in the fluid volume. An adequately large expansion chamber will respond to fluid volume changes with relatively little distension or contraction of the chamber. However, the desirability of a large expansion chamber runs counter to favored design characteristics of the probe itself, which are that the probe should be made as small and light as possible.

In accordance with one aspect of the present invention, an expansion chamber for an ultrasonic transducer probe is provided which is large enough to accommodate large variations in fluid volume while at the same time being arranged to permit a compact probe design. This is accomplished by emplacing the air bladder 100 expansion chamber completely within the fluid chamber of the probe. Unlike prior art expansion chambers, there is no wasted space resulting from the use of a separate volume of the probe solely for the expansion chamber. Neither is a wall of the expansion chamber outside the fluid chamber of the probe and connecting to the atmosphere. The volume encompassed by the air bladder 100 expansion chamber provides the benefit of accommodating significant temperature changes without causing any change in the exterior volume or overall dimensions of the probe 10.

In accordance with the preceding discussion, the present invention will be seen to have separate and severable aspects relating to a mechanical linkage for coupling a reciprocating element of a linear motor to a pivoting transducer head, an i improved linear motor employing a coil as a reciprocating element, an improved electrical connection to a pivotable transducer head, an improved electrical connection to a reciprocating coil element within a linear motor, an improved air bladder entirely within the fluid chamber of an ultrasonic probe, and other aspects. These aspects are readily susceptible to modification and/or recombination by a practitioner in the art of accousto-mechanical systems. For example, once it is realized that the temperature-compensating cylindrical air bladder may be entirely within the fluid chamber, and once it is considered that the cylindrical linear motor is also within the air chamber, then an attempt can be made to integrate the structures of the cylindrical linear motor and cylindrical air bladder. For example, this integration might be accomplished essentially by sealing, air-tight, the cylindrical linear motor, thereby allowing for its volumetric change, while still communicating electrical energy and mechanical force, particularly by using membranes or the like.

Figure 15:
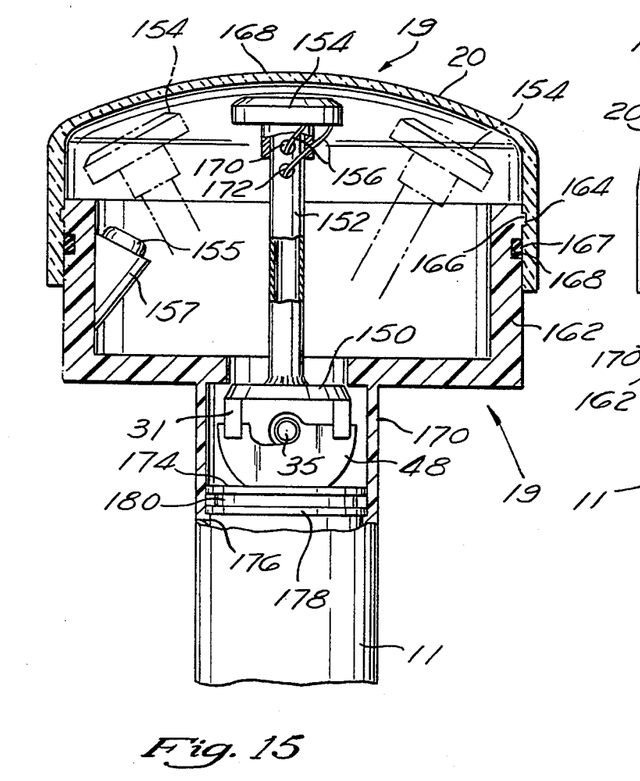
FIG. 15 is an enlarged view, partially in cross-section, of the head showing the imaging ultrasonic transducer mounted upon the extension.
Figure 16:
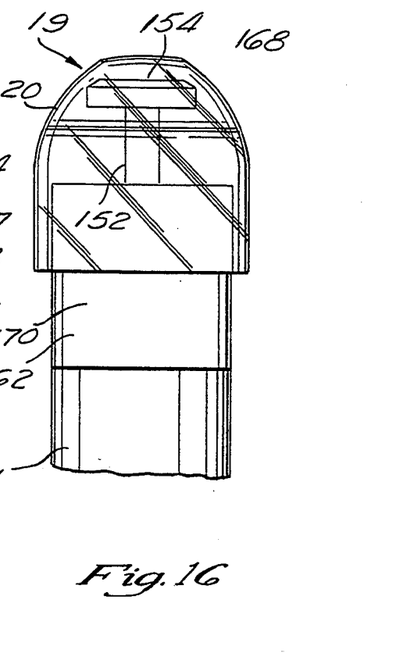
FIG. 16 is a side view of the head 19 of the ultrasonic peripheral vascular probe assembly of the present invention.

Referring now to FIGS. 15 and 16, the head 19 of the ultrasonic peripheral vascular probe assembly of the present invention is illustrated.

An elongate ultrasonic transparent window 168 is formed in the cap 20 to facilitate transmission of ultrasonic energy or radiation from imaging ultrasonic transducer 154 to the anatomical portion of the patient being scanned. Fluid contained with the cap 20 surrounds the imaging ultrasonic transducer 154 and facilitates transmission of ultrasonic energy from the imaging ultrasonic transducer 154 to the window 168.

The cap 20 is formed in an elongate fashion and comprises a smooth, slightly arched upper surface configured to comfortably and conveniently contact the patient. The cap 20 snaps onto the head housing 162 by inserting the cap 20 thereover such that the male detents 164 of the headhousing 162 engage and are received within the female detents 166 of the cap 20. Those skilled in the art will recognize that various other means for leak-free attachment are likewise suitable. The neck 170 of the cap 20 forms a circular opening which abuts and seals against complimentary upper surface 174 of the housing 11. The head 19 preferably attaches to the housing 11 via detents 176 which snap behind corresponding detents 178 formed upon the housing 11. Those skilled in the art will recognize that various other means for attachment are likewise suitable.

An O-ring seal 167 or the like may optionally be utilized to prevent leakage of the fluid from intermediate the cap 20 and the head housing 162. Similarly, an O-ring may optionally be disposed in a groove 180 formed at the upper end of the housing 11 so as to prevent leakage of the fluid intermediate the neck 170 of the head housing 162 and the housing 11. The handle 12 receives the lower portion of housing 11 into bore 26 (as shown in FIG. 2) thereof.

The scanning ultrasonic transducer 154 is disposed atop post or extension 152. The extension 152 is preferably formed of a lightweight metal such as aluminum, magnesium, or titanium. Those skilled in the art will recognize that various other lightweight materials are likewise suitable.

As discussed above, the extension 152 is formed upon base 150 which is configured to pivot reciprocally about the pivot pin 35 such that the scanning or imaging transducer 154 moves along an arc, preferably of approximately 50 degrees and preferably having a radius of approximately 40 mm and an arc length of approximately 35 mm.

By positioning the scanning transducer 16 a sufficient distance from the pivot axis, defined by pivot pin 35, the arc traveled by the imaging transducer 154 approximates straight line or linear motion such that movement of the imaging transducer 154 may be essentially along an elongate anatomical structure rather than merely at a comparatively small portion thereof as in prior art devices. That is, the imaging ultrasonic transducer 154 of the present invention tends to move back and forth along a line whereas in prior art devices the transducer merely pivots about a point and thus remains comparatively stationary. Thus, for the purposes of ultrasonic imaging, the path followed by the scanning ultrasonic transducer of the present invention is a substantially straight one.

In prior art devices the scanning ultrasonic transducer is positioned close, i.e. approximately 5–10 mm, to the pivot axis. Thus movement of the scanning ultrasonic transducer is confined to a very limited area, essentially being slight pivoting or rocking about a pivot. In contrast, the imaging ultrasonic transducer 154 of the present invention moves reciprocally along a comparatively long arc which is approximately 35–40 mm from end to end. The scanning ultrasonic transducer 16 of the present invention thus covers a considerable area suitable for imaging of elongate anatomical structures, i.e. peripheral blood vessels, etc.

A doppler transducer 155 is optionally fixedly mounted upon a support 157 within the head 19, so as to provide an indication of flow rates through various anatomical vessels.

Conductors 156 extend from the imaging ultrasonic transducer 154 and through first 170 and second 172 apertures formed in the extension 152. The conductors 156 extend through the hollow extension 152 and into the housing 11. The position sensor 48 provides an indication of the angular position of the imaging transducer 154, as described above.

Having thus described the structure of the ultrasonic peripheral vascular probe assembly of the present invention, a discussion of the operation thereof may be beneficial. Reciprocation of the coil assembly 81 of the linear motor assembly 60 results in movement of the imaging ultrasonic transducer 154 along an arc. The arc extends through the radiation path of the optional doppler ultrasonic transducer, if utilized. Thus, the optional doppler ultrasonic transducer provides flow information only when the imaging ultrasonic transducer 154 is not disposed within the radiation path thereof.

Thus, to use the ultrasonic peripheral vascular probe assembly of the present invention, it is positioned in contact with the patient over the anatomical structure to be imaged such that the imaging ultrasonic transducer 154 moves along the longitudinal axis of the anatomical structure. Such positioning permits the present invention to effectively image over a greater area, generally elongate in configuration, than prior art devices. Thus, an image of the elongate anatomical structure, as well as measurement of fluid flow therethrough is simultaneously provided by the present invention.

It is understood that the exemplary ultrasonic peripheral vascular probe assembly of the present invention described herein and shown in the drawings represents only a presently preferred embodiment of the invention. Indeed, various modifications and additions may be made to such embodiment without departing from the spirit and scope of the invention. For example, the scanning ultrasonic transducer can be configured and mounted in various ways to cause its motion to approximate straight line of linear motion. Indeed, its motion need not even be rotational pivotal. Rather various linear or generally linear motions are likewise suitable. Additionally, the cap may assume various configurations which reflect the motion of the scanning ultrasonic transducer and which minimize contact with the patient. Thus, these and other modifications and additions may be obvious to those skilled in the art and may be implemented to adapt the present invention for use in a variety of different applications.

What is claimed is:

1. A method for ultrasonically imaging elongate anatomical structures, the method comprising the steps of:
   a) moving an imaging ultrasonic transducer in a periodic fashion, the imaging ultrasonic transducer imaging an anatomical structure and periodically obstructing the path of a doppler ultrasonic transducer; and
   b) periodically measuring fluid flow within the anatomical structure with the doppler ultrasonic transducer when the doppler ultrasonic transducer is not obstructed by the imaging ultrasonic transducer.

2. An ultrasonic probe comprising:
   a) a housing;
   b) a base pivotally mounted within said housing;
   c) an elongate extension formed upon said base;
   d) an imaging ultrasonic transducer formed upon said extension such that said imaging ultrasonic transducer is constrained to move along an arc defined by said extension as said base pivots, said arc being of sufficient radius to approximate a straight line so as to facilitate imaging of elongate anatomical structures.

3. The ultrasonic probe as recited in claim 2 wherein the length of the arc along which said imaging ultrasonic transducer moves is between approximately 35 to 40 mm.

4. The ultrasonic probe as recited in claim 2 wherein the radius of the arc along which said imaging ultrasonic transducer moves is approximately 40 mm.

5. The ultrasonic probe as recited in claim 2 wherein the arc along which said imaging ultrasonic transducer moves extends for approximately 50 degrees.

6. An ultrasonic probe comprising:
   a) a housing;
   b) an imaging ultrasonic transducer movably mounted within said housing, said imaging ultrasonic transducer constrained to move along a path generally approximating a straight line to facilitate imaging of an elongate anatomical structure; and
   c) a doppler ultrasonic transducer having a radiation path, for measuring fluid flow through the anatomical structure simultaneously with imaging thereof.

7. The ultrasonic probe as recited in claim 6 wherein said doppler ultrasonic transducer is positioned such that said imaging ultrasonic transducer obscures said doppler ultrasonic transducer's radiation path during a portion of the imaging ultrasonic transducer's movement.

8. An ultrasonic probe comprising:
   a) an imaging ultrasonic transducer for imaging anatomical structures;
   b) a motor mechanically communicating movement to said imaging ultrasonic transducer in a periodic fashion;
   c) a fixed doppler ultrasonic transducer having a radiation path for measuring fluid flow utilizing the doppler effect; and
   d) wherein said moving imaging ultrasonic transducer is periodically disposed within the radiation path of said fixed doppler ultrasonic transducer and is periodically disposed outside the radiation path of said fixed doppler ultrasonic transducer, said fixed doppler ultrasonic transducer functioning to measure fluid flow only when said moving imaging ultrasonic transducer is disposed outside the radiation path of said fixed doppler ultrasonic transducer.

9. A method for ultrasonically imaging elongate anatomical structures, the method comprising the steps of:
   a) moving an imaging ultrasonic transducer in an arc having a sufficient radius to cause the movement of the imaging ultrasonic transducer to approximate linear motion for imaging purposes;
   b) positioning the imaging ultrasonic transducer proximate an elongate anatomic structure to be imaged;
   c) transmitting ultrasonic radiation from the imaging ultrasonic transducer to the elongate structure to be imaged and receiving ultrasonic radiation reflected from the elongate structure back to the imaging ultrasonic transducer;
   d) measuring fluid flow through the elongate anatomical structure with a doppler ultrasonic transducer, the radiation path of said doppler ultrasonic transducer being blocked by said imaging ultrasonic transducer during a portion of its movement along the arc; and
   e) wherein movement of the ultrasonic transducer along an arc having such a radius facilitates imaging of such elongate anatomical structures.

* * * * *